United States Patent
Aurbach et al.

(10) Patent No.: US 11,111,160 B2
(45) Date of Patent: Sep. 7, 2021

(54) ASYMMETRIC ELECTROCHEMICAL CELL APPARATUS, AND OPERATING METHODS THEREOF

(71) Applicant: Bar-Ilan University, Ramat Gan (IL)

(72) Inventors: Doron Aurbach, Bnei Brak (IL); Eran Avraham, Petach Tikva (IL); Izaak Cohen, Petach Tikva (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 159 days.

(21) Appl. No.: 15/753,717

(22) PCT Filed: Aug. 25, 2016

(86) PCT No.: PCT/IB2016/055079
§ 371 (c)(1),
(2) Date: Feb. 20, 2018

(87) PCT Pub. No.: WO2017/064577
PCT Pub. Date: Apr. 20, 2017

(65) Prior Publication Data
US 2018/0237317 A1   Aug. 23, 2018

Related U.S. Application Data

(60) Provisional application No. 62/209,399, filed on Aug. 25, 2015.

(51) Int. Cl.
*C25B 11/02* (2021.01)
*C02F 1/461* (2006.01)
(Continued)

(52) U.S. Cl.
CPC ............ *C02F 1/4618* (2013.01); *C01B 11/04* (2013.01); *C01B 11/06* (2013.01); *C02F 1/467* (2013.01);
(Continued)

(58) Field of Classification Search
CPC ......... C25B 11/02; C25B 9/18; C25B 11/035; C25B 11/12; C25B 15/00; C25B 1/06; C25B 9/12
(Continued)

(56) References Cited

U.S. PATENT DOCUMENTS 5,762,779 A    6/1998  Shiramizu
2007/0138020 A1  6/2007  Balagopal
(Continued)

FOREIGN PATENT DOCUMENTS

EP    0823400 A1    2/1998
JP    2000-79392 A   3/2000
(Continued)

OTHER PUBLICATIONS

Communication and Supplementary European Search Report for European application No. 16855018.4, dated May 29, 2019 (6 pages).
(Continued)

*Primary Examiner* — Zulmariam Mendez
(74) *Attorney, Agent, or Firm* — Roach Brown McCarthy & Gruber; Kevin D. McCarthy

(57) ABSTRACT

Asymmetric electrochemical cell apparatus, and methods of operating such apparatus to produce electrolyzed water.

10 Claims, 12 Drawing Sheets

(51) Int. Cl.
- *C01B 11/04* (2006.01)
- *C25B 1/26* (2006.01)
- *C01B 11/06* (2006.01)
- *C25B 15/02* (2021.01)
- *C02F 1/467* (2006.01)
- *C25B 9/17* (2021.01)
- *C25B 11/057* (2021.01)
- *C25B 15/08* (2006.01)

(52) U.S. Cl.
CPC .................. *C25B 1/26* (2013.01); *C25B 9/17* (2021.01); *C25B 11/057* (2021.01); *C25B 15/02* (2013.01); *C25B 15/08* (2013.01); *C02F 1/46109* (2013.01); *C02F 2001/4619* (2013.01); *C02F 2001/46133* (2013.01); *C02F 2001/46185* (2013.01); *C02F 2201/4618* (2013.01); *C02F 2209/06* (2013.01); *C02F 2307/02* (2013.01)

(58) Field of Classification Search
USPC ......................................................... 204/280
See application file for complete search history.

(56) References Cited

U.S. PATENT DOCUMENTS

| | | | |
|---|---|---|---|
| 2007/0186367 A1* | 8/2007 | Field ................... | A47L 11/4011 15/320 |
| 2015/0001066 A1* | 1/2015 | Joshi ........................ | C25B 1/26 204/248 |
| 2015/0034496 A1 | 2/2015 | Kawazu et al. | |
| 2015/0298998 A1* | 10/2015 | Legzdins ............ | C02F 1/46104 205/748 |
| 2016/0264599 A1 | 9/2016 | Warner et al. | |

FOREIGN PATENT DOCUMENTS

| | | |
|---|---|---|
| JP | 3174882 U | 4/2012 |
| JP | 2012115749 A | 6/2012 |
| KR | 20130082118 A | 7/2013 |
| WO | 2013/019427 A1 | 2/2013 |
| WO | 2014001177 A1 | 1/2014 |

OTHER PUBLICATIONS

International Search Report from PCT/IB2016/055079, 4 pages, dated Nov. 30, 2016.

* cited by examiner

FIG. 5A
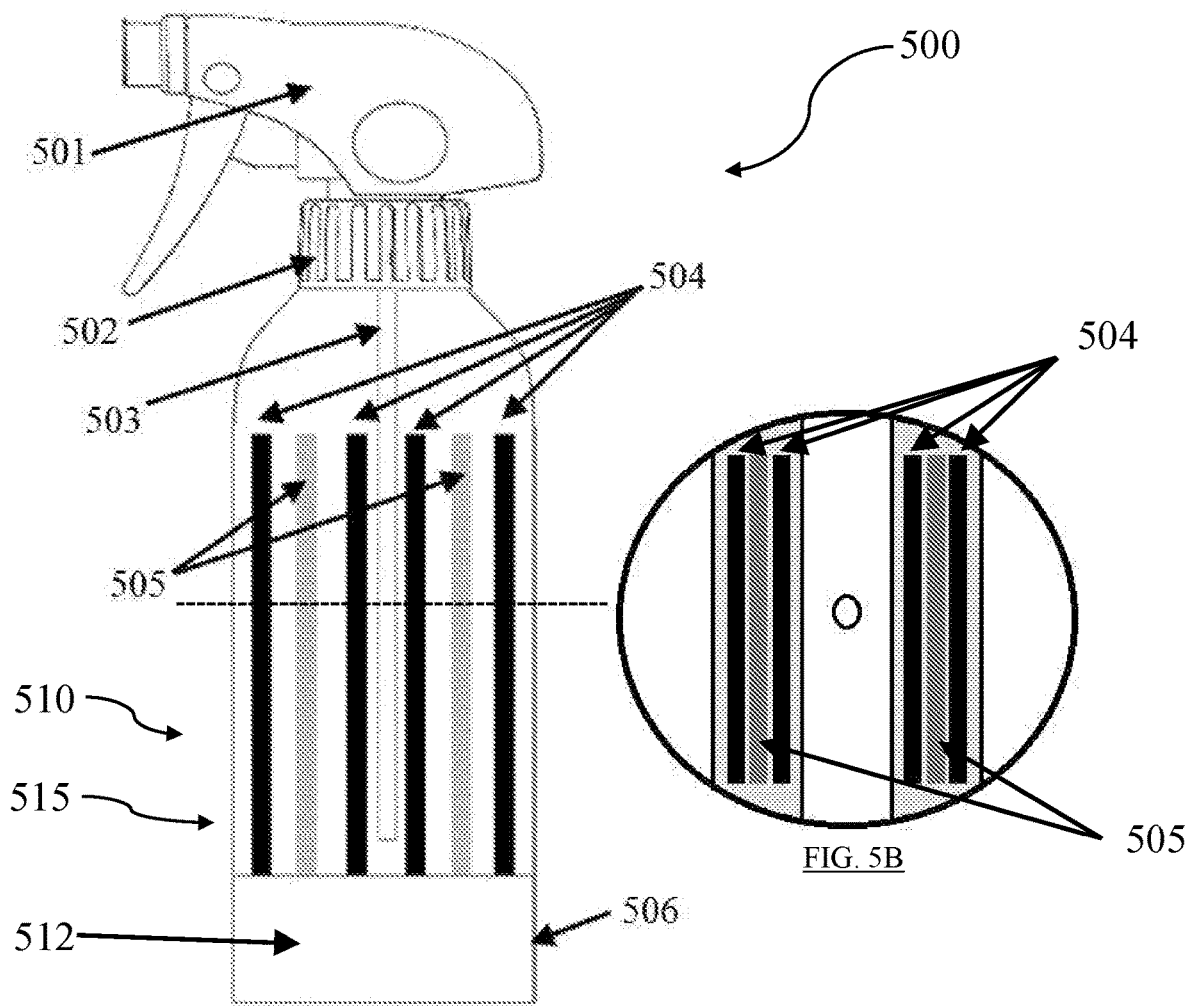
FIG. 5B
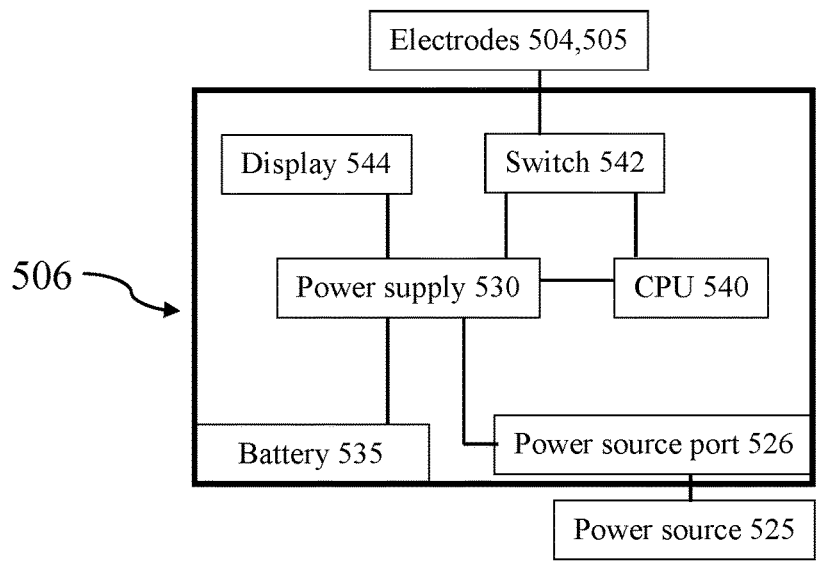
FIG. 5C

FIG. 15A
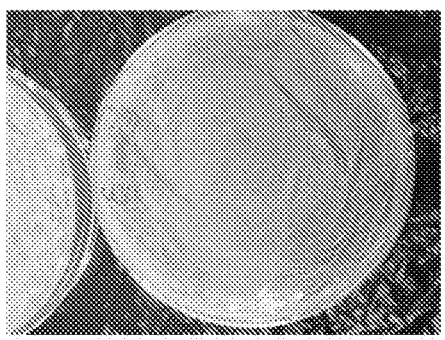
Escherichia coli, initial
FIG. 15B
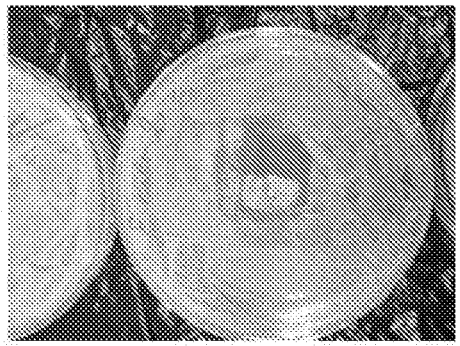
After 24Hr
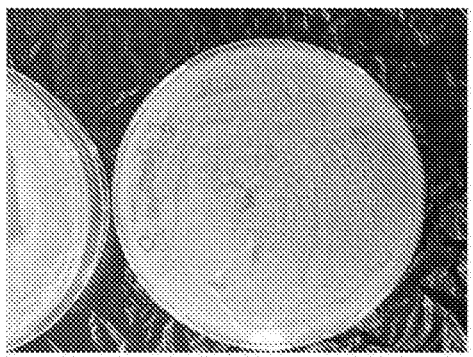
Staphylococcus aureus, initial
FIG. 16A
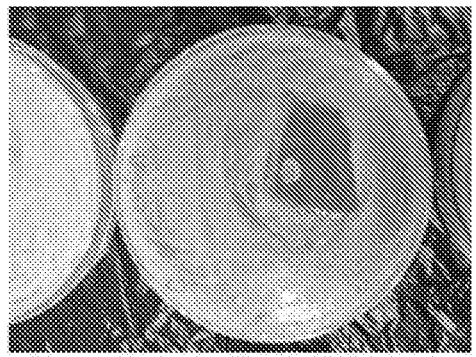
After 24Hr
FIG. 16B

ASYMMETRIC ELECTROCHEMICAL CELL APPARATUS, AND OPERATING METHODS THEREOF

This application draws priority from U.S. Provisional Patent Application Ser. No. 62/209,399, filed Aug. 25, 2015, which is incorporated by reference for all purposes as if fully set forth herein.

FIELD AND BACKGROUND OF THE INVENTION

The present invention relates to asymmetric electrochemical cell apparatus, and methods of operating such apparatus to produce electrolyzed water.

FIG. 1 is a schematic illustration of a two-compartment electrochemical cell having an ion-exchange membrane 108 for producing electrolyzed water, according to a prior art process. Salt water (aqueous NaCl) feed 109A, 109B is introduced to each compartment of the cell.

When electrically connected to a suitable power supply 101, the reactions which take place over the electrodes may be represented as follows: at the positive electrode (anode) 106:

$$2H_2O \rightarrow 4H^+ + O_2 + 4e^-$$

$$2NaCl \rightarrow Cl_2 + 2Na^+ + 2e^-$$

$$Cl_2 + H_2O \rightarrow HCl + HOCl$$

and at the negative electrode (cathode) 107:

$$2H_2O + 2e^- \rightarrow 2OH^- + H_2.$$

At the positive electrode, water is electrolyzed to form hydrogen ions and oxygen. Chloride forms chlorine, which reacts with water to form HCl and HOCl, which typically discharge 102 from the acidic compartment 104 of the cell at a pH within a range of 2-6. The membrane allows the transfer of cations such as $Na^-$, which traverses the membrane and enters the negative compartment 105 of the cell. At the negative electrode, hydroxide ($OH^-$) is liberated, and hydrogen is evolved. The discharge 103 from the negative compartment may contain $NaOH_{(aq)}$, and typically has a pH of 8-13.

Such electrochemical cells require a membrane, and typically require two expensive electrodes (e.g., based on titanium alloys and pure graphite) that may be largely inert in the harsh electrolytic conditions.

Thus, the present inventors have recognized a need for improved apparatus and methods for producing electrolyzed water.

SUMMARY OF THE INVENTION

According to some teachings of the present invention, there is provided, in an asymmetric electrochemical cell having a positive electrode and a negative electrode, an electrochemical capacitance ratio ($R_{ec}$) of the negative electrode to the positive electrode being at least 7:1, an electrochemical method of producing a hypohalous acid (HOX) in an aqueous solution containing: (I) alkali metal cations ($M^+$); and (II) halogen anions ($X^-$) corresponding to the hypohalous acid, the method comprising: (a) in a first, semi-capacitive electrochemical stage, with the positive and negative electrodes immersed in the aqueous solution, applying a first electrical current between the positive and negative electrodes, such that: (i) a portion of said alkali metal cations is adsorbed on a surface of the negative electrode in a capacitive mode, and (ii) the positive electrode produces the hypohalous acid from the halogen anions, via a halogen intermediate, and liberates hydrogen ions ($H^+$); and subsequently, (b) applying a second electrical current between the positive and negative electrodes, in a second process stage, to produce the hypohalous acid in the aqueous solution, the aqueous solution having a pH of at most 4, or within a range of 2.0 to 4.0.

According to another aspect of the present invention there is provided an asymmetric electrochemical cell for producing a hypohalous acid (HOX) in a product solution containing alkali metal cations ($M^+$) and halogen anions ($X^-$) corresponding to the hypohalous acid, the asymmetric electrochemical cell comprising: (a) at least a first electrode; (b) at least a second electrode; wherein an electrochemical capacitance ratio ($R_{ec}$) of said at least a first electrode to said at least a second electrode is at least 7:1; (c) a vessel containing said first and second electrodes, and structured so as to enable, at least in first and second operative modes, immersion of said first and second electrodes in an aqueous solution contained by said vessel; (d) a processor; and (e) a power supply, responsive to said processor, said power supply adapted to apply, between said first and second electrodes, a first electrical current during said first operative mode, and a second electrical current during said second operative mode, so as to form, via said aqueous solution, an electrical circuit; whereby, when an initial aqueous solution contains a total concentration of at least 150 ppm of the alkali metal cations ($M^+$) and halogen anions ($X^-$), said first electrical current causes a portion of said alkali metal cations to be adsorbed on a surface of said first electrode in a capacitive mode, and said second electrical current causes said second electrode to produce the hypohalous acid from the halogen anions, via a halogen intermediate, and to liberate hydrogen ions ($H^+$); said processor adapted to control operation of the electrochemical cell whereby, upon completion of said second operative mode, the product solution containing the hypohalous acid has a pH of at most 4, or within a range of 2.0 to 4.0.

According to another aspect of the present invention there is provided an asymmetric electrochemical cell for producing a hypohalous acid (HOX) in a product solution containing alkali metal cations ($M^+$) and halogen anions ($X^-$) corresponding to the hypohalous acid, the asymmetric electrochemical cell comprising: (a) at least a first electrode; (b) at least a second electrode; wherein an electrochemical capacitance ratio ($R_{ec}$) of said at least a first electrode to said at least a second electrode is at least 7:1; (c) a vessel containing said first and second electrodes, and structured so as to enable, at least in a first operative mode, immersion of said first and second electrodes in an aqueous solution contained by said vessel; (d) a processor; and (e) a power supply, responsive to said processor, said power supply adapted to apply, between said first and second electrodes, a first electrical current during said first operative mode, so as to form, via said aqueous solution, an electrical circuit; whereby, when an initial aqueous solution contains a total concentration of at least 150 ppm of the alkali metal cations ($M^+$) and halogen anions ($X^-$), said first electrical current causes a portion of said alkali metal cations to be adsorbed on a surface of said first electrode in a capacitive mode, and said second electrical current causes said second electrode to produce the hypohalous acid from the halogen anions, via a halogen intermediate, and to liberate hydrogen ions ($H^+$); said processor adapted to control operation of the electrochemical cell whereby the product solution containing the hypohalous acid has a pH of at most 4, or within a range of 2.0 to 4.0, and wherein optionally, said power supply is further adapted to apply, between said first and second electrodes, in a second (preceding or subsequent) operative mode, a second electrical current, having a reversed polarity with respect to said first operative mode, such that the first electrode operates in a substantially capacitive mode, while the second electrode operates in a substantially faradaic mode.

According to yet another aspect of the present invention there is provided an electrochemical towel for producing electrolyzed water, the electrochemical towel comprising: (a) at least a first electrode layer; (b) at least a second electrode layer; wherein an electrochemical capacitance ratio ($R_{ec}$) of said at least a first electrode to said at least a second electrode is at least 7:1; (c) an electrically insulating layer disposed in between said first electrode layer and said second electrode layer; at least one of said first electrode layer, said electrically insulating layer, and said second electrode layer adapted to absorb water; (d) a processor; and (e) a power supply, responsive to said processor, said processor and said power supply adapted to apply, between said first and second electrode layers, a first electrical current during a first operative, capacitive mode, having a first polarity, and a second electrical current during a second operative, capacitive mode, having an opposite polarity, with respect to said first polarity, so as to form, when a first aqueous solution is absorbed within the towel, an electrical circuit; whereby, when said first aqueous solution contains a total concentration of at least 150 ppm of the alkali metal cations ($M^+$) and halogen anions ($X^-$), said first electrical current causes a portion of said alkali metal cations to be adsorbed on a surface of said first electrode layer in said first operative capacitive mode, so as to produce a hypohalous acid (HOX) from the halogen anions, via a halogen intermediate, and to liberate hydrogen ions ($H^+$); and wherein said second electrical current having said opposite polarity causes said first electrode layer, in said second operative, capacitive mode, to produce a hypohalite ($OX^-$) in an alkaline medium.

According to yet another aspect of the present invention there is provided an asymmetric electrochemical cell for producing a hypohalous acid (HOX) in a product solution containing alkali metal cations ($M^+$) and halogen anions ($X^-$) corresponding to the hypohalous acid, the asymmetric electrochemical cell comprising: (a) at least a first electrode; (b) at least a second electrode; wherein an electrochemical capacitance ratio ($R_{ec}$) of said at least a first electrode to said at least a second electrode is at least 7:1; (c) a vessel containing said first and second electrodes, and structured so as to enable, at least in first and second operative modes, immersion of said first and second electrodes in an aqueous solution contained by said vessel; (d) a processor; and (e) a power supply, said processor and said power supply adapted to apply, between said first and second electrodes, a first electrical current during said first operative mode, and a second electrical current during said second operative mode, so as to form, via said aqueous solution, an electrical circuit; whereby, when an initial aqueous solution contains a total concentration of at least 150 ppm of the alkali metal cations ($M^+$) and halogen anions ($X^-$), said first electrical current causes a portion of said alkali metal cations to be adsorbed on a surface of said first electrode in a capacitive mode to produce the hypohalous acid from the halogen anions, via a halogen intermediate, and to liberate hydrogen ions ($H^+$); and wherein said processor and said power supply are further adapted to apply, between said first and second electrodes, a second electrical current during second operative mode, said second electrical current having an opposite polarity with respect to said first electrical current, such that said first electrode, in said second operative mode, operates in a capacitive fashion to produce a hypohalite ($OX^-$) in an alkaline medium.

According to further features in the described preferred embodiments, the asymmetric electrochemical cell is disposed in a container having a volume of at least 300 ml, at least 500 ml, at least 1000 ml, or at least 2000 ml, and optionally, at most 10000 ml, at most 5000 ml, at most 4000 ml, or at most 3000 ml.

According to still further features in the described preferred embodiments, the asymmetric electrochemical cell is disposed in a container having a volume of within a range of 300 ml to 10000 ml, 300 ml to 5000 ml, or 500 ml to 5000 ml.

According to still further features in the described preferred embodiments, the applying of said second electrical current is initiated after a pH of the aqueous solution produced in said first stage is within a range of 2.0 to 4.0.

According to still further features in the described preferred embodiments, said applying of said second electrical current is initiated after a pH of the aqueous solution produced in said first stage has stabilized within a range of 2.0 to 4.0.

According to still further features in the described preferred embodiments, said pH of the aqueous solution in said first stage is at least 2.2, at least 2.4, at least 2.5, or at least 2.6.

According to still further features in the described preferred embodiments, said pH of the aqueous solution in said first stage is at most 3.8, at most 3.6, at most 3.4, or at most 3.2.

According to still further features in the described preferred embodiments, the method further comprises, subsequently to (b), utilizing the aqueous solution produced in (b) to treat acne, and/or as a skin disinfectant.

According to still further features in the described preferred embodiments, the method further comprises, subsequently to (b), utilizing the aqueous solution produced in (b) to at least one of: dissolve scale, reduce or eradicate biofilm, and disinfect inanimate surfaces.

According to still further features in the described preferred embodiments, the method further comprises, subsequently to (b), replenishing the asymmetric electrochemical cell with a solution containing a dissolved alkali halide.

According to still further features in the described preferred embodiments, the method further comprises, subsequently to said replenishing, operating the asymmetric electrochemical cell by reversing a polarity between the positive and negative electrodes, such that the previously negative electrode, which is now a positively polarized electrode, desorbs said alkali metal cations and adsorbs said halide, and the previously positive electrode, which is now a negatively polarized electrodes, producing a basic solution containing a hypohalite ($OX^-$) corresponding to said halide.

According to still further features in the described preferred embodiments, the method further comprises utilizing said basic solution for at least one of degreasing and pesticide removal.

According to still further features in the described preferred embodiments, the method further comprises, subsequently to said producing of said basic solution: removing or completely removing said basic solution from the asymmetric electrochemical cell, so as to complete a regeneration of the negative electrode; replenishing the asymmetric electrochemical cell with a solution containing a dissolved alkali halide; and operating the asymmetric electrochemical cell to produce a hypohalous acid in an aqueous solution having a pH within a range of 2.0 to 4.0.

According to still further features in the described preferred embodiments, the method further comprises, subsequently to (b), rinsing the negative electrode with water, followed by drying the negative electrode, so as to regenerate the negative electrode.

According to still further features in the described preferred embodiments, the total concentration of said alkali metal cations and said halogen anions in the aqueous solution, or within feed water used in preparing the aqueous solution, is within a range of 150 to 2000 ppm, 150 to 1500 ppm, 150 to 1000 ppm, 150 to 800 ppm, 150 to 600 ppm, 200 to 800 ppm, 200 to 600 ppm, or 200 to 500 ppm.

According to still further features in the described preferred embodiments, the aqueous solution consists of, or consists essentially of, tap water.

According to still further features in the described preferred embodiments, the initial concentration of said halogen anions is at most 1M, and optionally, within a range of 0.01M to 1M, 0.1M to 2M, or 0.1M to 1M.

According to still further features in the described preferred embodiments, the at least one of said first current and said second current is applied such that a voltage across the positive and negative electrodes is at most 5V, at most 4.5V, or at most 4V, and optionally, within a range of 2-4V.

According to still further features in the described preferred embodiments, the second current is at most 25%, at most 20%, at most 15%, or at most 12% of said first current.

According to still further features in the described preferred embodiments, the asymmetric electrochemical cell further comprises a switching mechanism, associated with said power supply, and adapted, in a third operative mode, to apply a third current between said first and second electrodes while reversing a polarity therebetween.

According to still further features in the described preferred embodiments, the processor is adapted to control said power supply such that with a solution containing alkali metal cations ($M^+$) and halogen anions ($X^-$) corresponding to the hypohalous acid, disposed in said vessel, said third current is sufficient to desorb said alkali metal cations that were adsorbed on said surface of said first electrode, and to adsorb said halogen anions, so as to produce an alkaline solution containing a hypohalite ($OX^-$).

According to still further features in the described preferred embodiments, the switching mechanism is responsive to said processor.

According to still further features in the described preferred embodiments, the first electrode includes, largely includes, or consists of, an activated carbon.

According to still further features in the described preferred embodiments, the second electrode includes, largely includes, at least one construct selected from the group consisting of a graphite sheet, a carbon cloth, a carbon paper, or a titanium sponge.

According to still further features in the described preferred embodiments, the electrochemical capacitance ratio ($R_{ec}$) is at least 10:1, at least 12:1, at least 15:1, at least 20:1, at least 30:1, at least 50:1, at least 100:1, or at least 250:1, and optionally, at most 1000, at most 800, at most 600, or at most 500.

According to still further features in the described preferred embodiments, the cell is a portable asymmetric electrochemical cell.

According to still further features in the described preferred embodiments, the cell is a membraneless asymmetric electrochemical cell.

According to still further features in the described preferred embodiments, the power supply and said processor are adapted to limit said first and second electrical currents whereby a voltage applied between said first and second electrodes is at most 5V, at most 4.5V, or at most 4V, and optionally, at least 2V, at least 2.5V, or at least 3V.

According to still further features in the described preferred embodiments, the processor is adapted to control said power supply such that second current is at most 25%, at most 20%, at most 15%, or at most 12% of said first current.

According to still further features in the described preferred embodiments, the asymmetric electrochemical cell is disposed within a spraying or dispensing device adapted to spray or dispense a liquid disposed within said vessel.

According to still further features in the described preferred embodiments, the asymmetric electrochemical cell is disposed within a spraying device adapted to spray the product solution disposed within said vessel.

According to still further features in the described preferred embodiments, the asymmetric electrochemical cell is disposed within a spraying device adapted to spray said alkaline solution disposed within said vessel.

According to still further features in the described preferred embodiments, the aqueous solutions produced are used for at least one of disinfecting skin, disinfecting household and industrial surfaces, disinfecting utensils, and disinfecting food agricultural produce such as fruit or vegetables.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 5A provides a schematic side view of an inventive electric sprayer having at least one high surface area electrode and having at least one low surface area electrode;

FIG. 5B provides a cross-section of the body of the inventive electric sprayer of FIG. 5A;

FIG. 5C provides a schematic representation of an electrical diagram of an inventive electrochemical device, such as the inventive electric sprayer of FIG. 5A;

FIGS. 15A and 16A are photographs of Escherichia coli (FIG. 15A) and Staphylococcus Aureus (FIG. 16A) colonies in Petri dishes, grown as reference colonies;

FIGS. 15B and 16B are photographs of Escherichia coli (FIG. 15B) and Staphylococcus Aureus (FIG. 16B) colonies following treatment in the central area of the dishes, using polarized mini-towels of the present invention;

DESCRIPTION OF THE PREFERRED EMBODIMENTS

Figure 1:
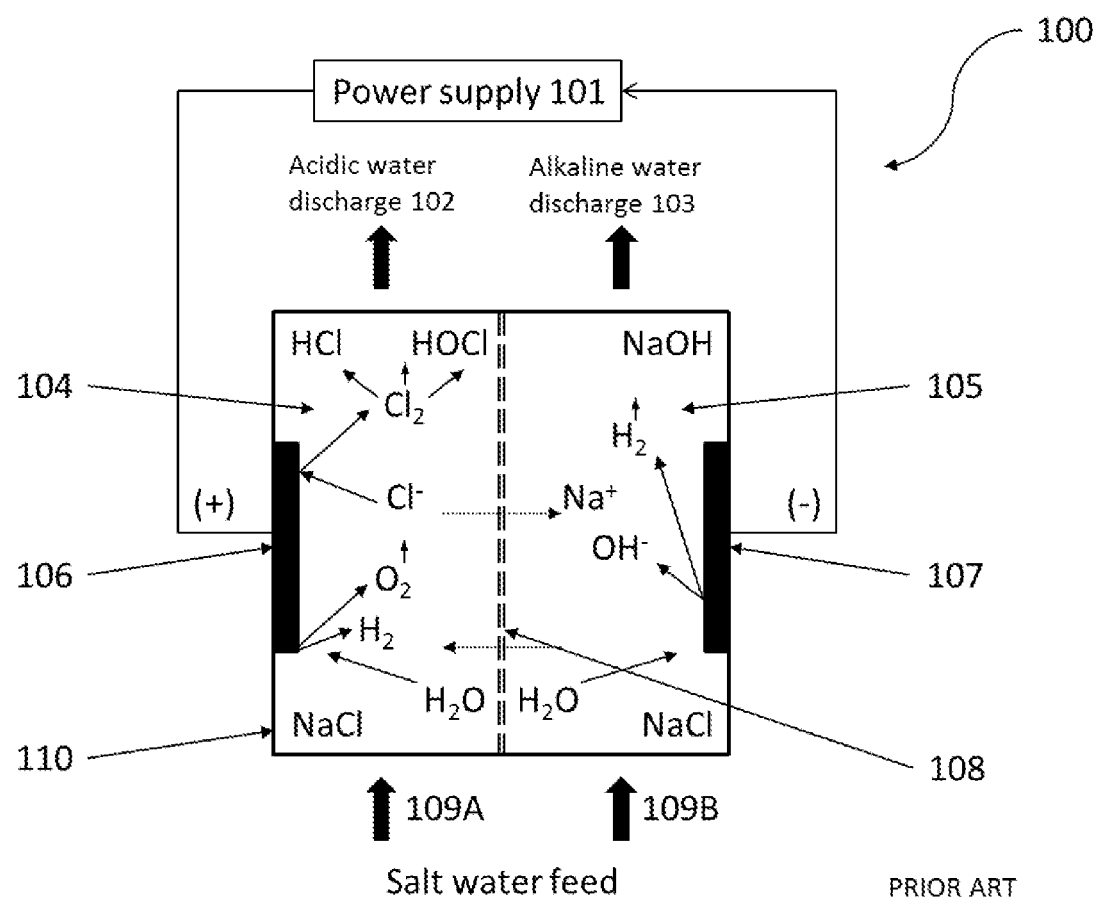
FIG. 1 is a schematic illustration of a two-compartment electrochemical cell having an ion-exchange membrane for producing electrolyzed water, according to the prior art.

The principles and operation of the asymmetric electrochemical cell technologies of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
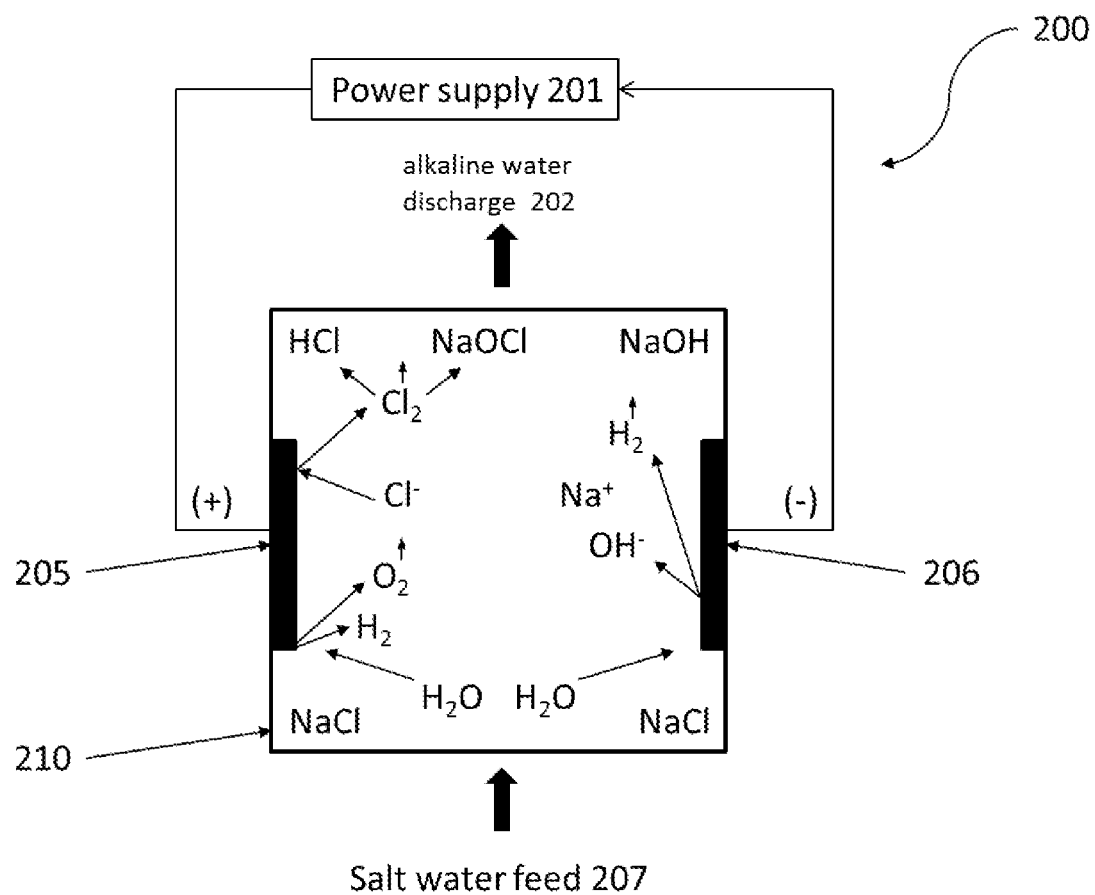
FIG. 2 is a schematic illustration of a single-compartment electrochemical cell for producing alkaline electrolyzed water.

With reference now to the drawings, FIG. 2 provides a schematic illustration of a single-compartment electrochemical cell for producing alkaline electrolyzed water 202. Salt water (aqueous NaCl) feed 207 is introduced to the cell. When positive electrode (anode) 205 and negative electrode (cathode) 206 are electrically connected to a suitable power supply 201, the faradaic reactions which take place over the electrodes ultimately result in an alkaline solution containing an alkali hypohalite (e.g., sodium hypochlorite) and having a pH of around 8-10.

Figure 3:
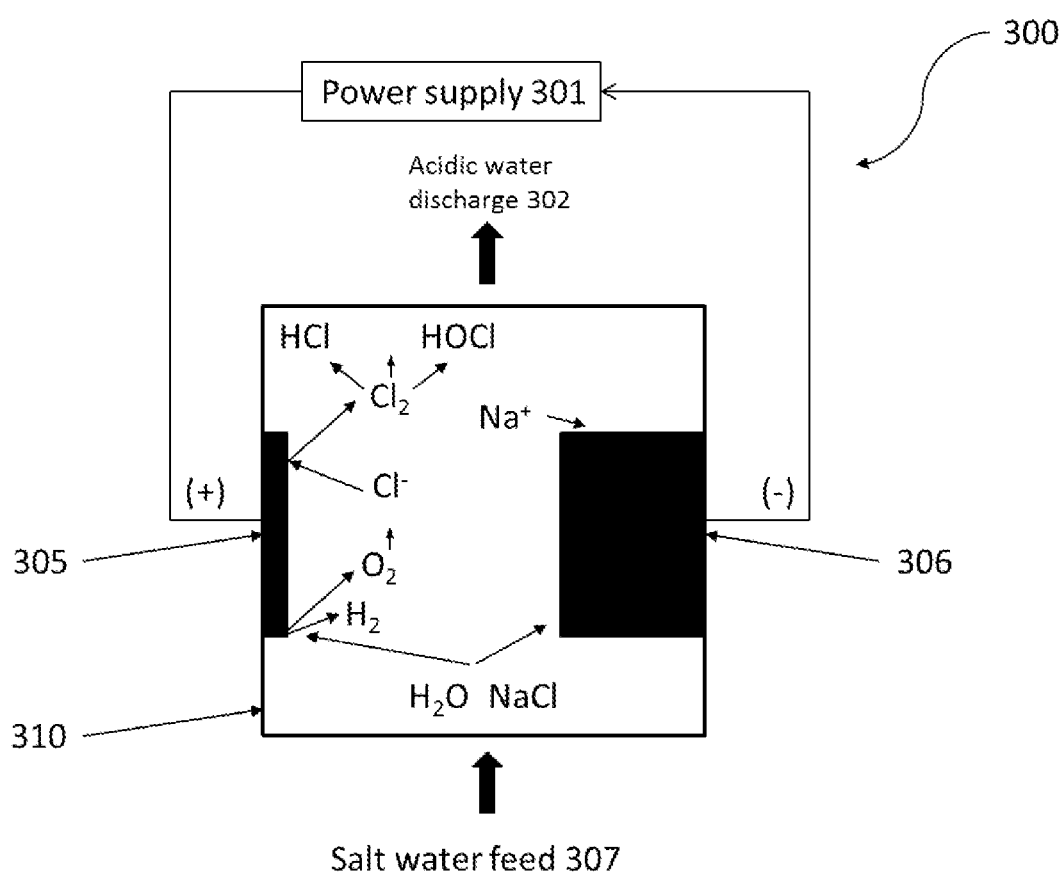
FIG. 3 is a schematic illustration of a single-compartment electrochemical cell for producing acidic electrolyzed water, according to an embodiment of the present invention.

FIG. 3 is a schematic illustration of an asymmetric, typically single-compartment electrochemical cell 300 for producing acidic electrolyzed water 302, according to an embodiment of the present invention. Electrochemical cell 300 includes a cell vessel or housing 310 adapted to contain at least one positive electrode 305 and at least one negative electrode 306. Positive electrode 305 and negative electrode 306 are electrically connected to a power supply 301, and with the water or aqueous solution disposed within cell housing 310, forms an electrical circuit.

The feed or operating solution 307 to asymmetric electrochemical cell 300 contains an alkali halide solute, typically Na⁺ or K⁺, and chloride (Cl⁻).

The inventors have discovered that asymmetric electrochemical cell 300, while having a structure similar to the electrochemical cell of FIG. 2, may advantageously be used to produce electrolyzed water having a pH within a range of 2.0 to 4.0. Electrolyzed water within this pH range is particularly efficacious from an anti-microbial standpoint.

One embodiment of the present invention is an electrochemical method of producing a hypohalous acid (HOX) in an aqueous solution containing: (I) alkali metal cations (M⁺); and (II) halogen anions (X⁻) corresponding to the hypohalous acid, the method comprising: (a) in a first, semi-capacitive electrochemical stage, with the positive and negative electrodes immersed in the aqueous solution, applying a first electrical current between the positive and negative electrodes, such that: (i) a portion of said alkali metal cations is adsorbed on a surface of the negative electrode in a capacitive mode, and (ii) the positive electrode produces the hypohalous acid from the halogen anions, via a halogen intermediate, and liberates hydrogen ions (H⁺); and subsequently, (b) applying a second electrical current between the positive and negative electrodes, in a second process stage, to produce the hypohalous acid in the aqueous solution, the aqueous solution having a pH within a range of 2.0 to 4.0. The second current is generally much lower than the first current.

In order to sufficiently reduce the pH of the aqueous solution to 4.0 or less during the first, semi-capacitive electrochemical stage, the electrochemical capacitance ratio ($R_{ec}$) of the negative electrode to the positive electrode being should be at least 3:1, at least 4:1, or at least 5:1, and more typically, at least 7:1, and more typically, at least 10:1, at least 12:1, at least 15:1, at least 20:1, at least 30:1, at least 50:1, at least 100:1, or at least 250:1. Typically, the $R_{ec}$ is at most 1000:1, at most 700:1, at most 500:1, or at most 400:1.

It will be appreciated that the lower pH to be attained ("target pH"), and/or the higher the initial pH of the feed solution, the larger the $R_{ec}$ or the differential between the electrochemical capacitance of the negative electrode and the electrochemical capacitance of the positive electrode ($\Delta_{ec}$).

Similarly, increasing the volume of the aqueous solution within the electrochemical cell may require a larger $R_{ec}$ and/or a larger $\Delta_{ec}$.

Figure 4:
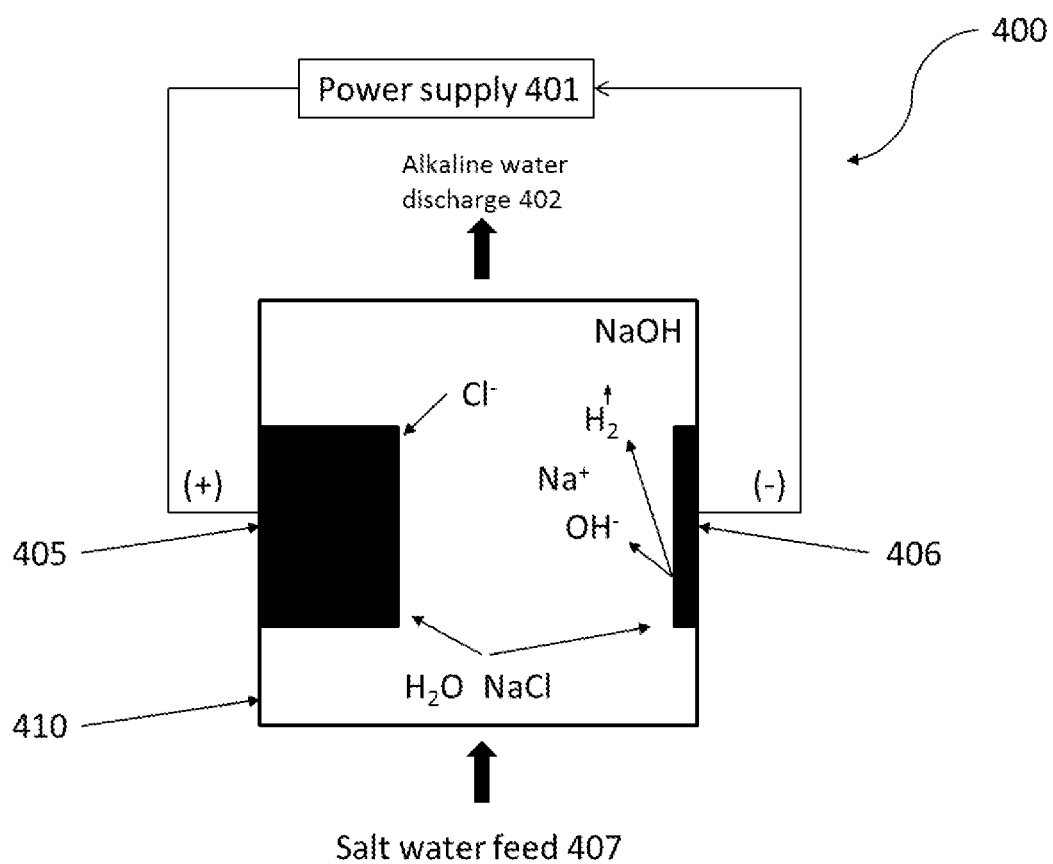
FIG. 4 is a schematic illustration of a single-compartment electrochemical cell for producing alkaline electrolyzed water, according to an embodiment of the present invention.

FIG. 4 is a schematic illustration of an asymmetric, typically single-compartment electrochemical cell 400 for producing alkaline electrolyzed water 402, according to an embodiment of the present invention. Electrochemical cell 400 includes a cell vessel or housing 410 adapted to contain at least one positive electrode 405 and at least one negative electrode 406. Positive electrode 405 and negative electrode 406 are electrically connected to a power supply 401, and with the water or aqueous solution disposed within cell housing 410, forms an electrical circuit.

The feed or operating solution 407 to asymmetric electrochemical cell 400 contains an alkali halide solute, typically $Na^+$ or $K^+$, and chloride ($Cl^-$).

Significantly, the asymmetry in asymmetric electrochemical cell 400 is the opposite of the asymmetry in asymmetric electrochemical cell 300 described hereinabove: the surface area, or electrochemical capacitance of positive electrode 405 is appreciably larger than that of the at least one negative electrode 406.

The inventors have discovered that asymmetric electrochemical cell 400, while having a structure similar to the electrochemical cell of FIG. 2, may advantageously be used to produce electrolyzed water having a much higher pH, for example, a pH of at least 10, at least 11, at least 12, or at least 13 or higher. Electrolyzed water at such an elevated pH is particularly efficacious in degreasing applications and in removing pesticides from goods and produce.

Various aspects of the present invention require solely one electrode (i.e., the low-surface area electrode) that is resistive to electrolysis reactions. For the high surface area electrode, relatively inexpensive materials such as activated carbon may advantageously be utilized. Moreover, the cell membrane used in prior-art processes is obviated.

FIG. 5A provides a schematic, transparent side view of an inventive electrochemical device or sprayer 500 that may include a vessel or bottle 510, and a spray head 501 connected to an immersion tube 503. Spray head 501 may be attached or secured to bottle 510 in various ways, typically by a threaded element 502 that screws on to a threaded neck (not shown) of bottle 510.

Within bottle 510 are disposed at least one high surface area electrode 504 and at least one low surface area electrode 505. Electrodes 504 and 505 may be arranged as sheets, typically substantially parallel sheets, disposed in a vertical orientation with respect to the side of bottle 510. Such an exemplary arrangement is shown in the cross-sectional representation of bottle 510, provided in FIG. 5B.

The electronics or electronics unit 506 of inventive electrochemical device or sprayer 500 may be housed in a separate compartment 512 at the bottom of bottle 510, fluidly sealed from a liquid-containing volume 515 of bottle 510.

A schematic exemplary electrical diagram of the electronics 506 of inventive electrochemical device or sprayer 500 is provided in FIG. 5C. In one embodiment, a power source 525, which is typically disposed externally to sprayer 500, may connect to the electronics 506 of sprayer 500 via a power source port 526 (e.g., a USB connection).

The electronics 506 typically include a power supply 530, which in some embodiments, is electrically connected to an on-board battery 535 via a battery housing.

Power supply 530 may be responsive to a processing unit, such as CPU 540, which is typically equipped with an internal memory, but alternatively or additionally, may communicate with an external memory. At least one switch 542, electrically connected to electrodes 504, 505, may be responsive to CPU 540, for example to turn the current to the electrodes on or off. In some embodiments, switch 542 may be manually operated.

A display 544 may also be responsive to CPU 540. In some embodiments, display 544 may have a first indicator (e.g., a LED light) for indicating that the cell is operating, and a second indicator for indicating that the desired pH has been obtained, such that the solution produced is ready for consumption.

To operate electrochemical sprayer 500, liquid-containing volume 515 of bottle 510 is filled with tap water containing at least 150 ppm alkali halide solute. Alternatively, any water source, even water containing less than 150 ppm alkali halide solute (e.g., distilled water, deionized water) may be used, simply by adding a portion of alkali halide salt such as table salt (NaCl). Alternatively, a pre-prepared solution of the alkali halide may be introduced.

Subsequently, an electrical current is delivered across electrodes 504 and 505.

Electrochemical sprayer 500 may be operated substantially as described hereinabove, particularly with respect to FIGS. 3 and 4. In one embodiment, electrochemical sprayer 500 is operated such that, in a first stage, the negative electrode operates in a capacitive mode, while the positive electrode operates in a faradaic mode, and subsequently, in a second stage, both the positive and negative electrodes operate in a faradaic mode to produce the hypohalous acid in the aqueous solution. A suitable relative electrochemical capacitance of the electrodes is implemented, and operation is controlled, so as to control the pH of the aqueous solution within a predetermined range. Typically, the aqueous solution produced by the cell has a pH within a range of 2.0 to 4.0. Yet more typically, the pH of the aqueous solution containing the hypohalous (e.g., hypochlorous) acid, produced by the cell, is at least 2.2, at least 2.4, at least 2.5, or at least 2.6, particularly for skin-cleansing applications. The electrochemical sprayer may be used to deliver the resultant disinfectant solution, to clean and disinfect a variety of surfaces, including human and mammal skin (e.g., as a liquid hand cleanser).

It will be appreciated that the alkali halide may be introduced to electrochemical sprayer 500 (as well as to other relevant electrochemical devices disclosed herein) in the form of a tablet or capsule, or in the form of a powder. It will be further appreciated that detergents, odorants, and other functional materials may be incorporated into the consumable salt.

The electrochemical spraying may be integrated with a conventional steam treatment, which may enhance the results of both processes.

The concentration of the produced hypochlorous acid thus formed depends on the volume of the solution within the electrochemical sprayer. This volume may be adjusted, within bounds, according to need. In one embodiment of the inventive method, the additional electrochemical capacitance required for the high-surface electrode generally increases linearly) with increasing solution volume within the cell.

Since at low pH, a portion of the hypochlorous acid and hydrochloric acid reverts to water and chlorine gas (as elaborated with reference to FIG. 9), it may be advantageous to continue the electrochemical activity of the $2^{nd}$ operating stage so as to replenish the hypochlorous acid.

Operation is now described in more detail, and in exemplary fashion. A power source is connected to the device, e.g., via a USB cable. When connecting the cell to the USB a voltage of up to about 5V and up to about 1A may be applied between the high surface-area electrodes and the low surface area electrodes. The high surface-area electrodes are negatively polarized and electrostatically filled with counter ions (e.g., $Na^+$ and/or $K^+$), in a capacitive manner. The low surface-area electrodes are positively polarized and create electrochemical interactions with the solution, which result in the production of hypochlorous acid and hydrochloric acid. The pH may be determined by, or strongly influenced by, the surface area of the high surface-area electrodes with respect to the low surface-area electrodes (or more precisely, the electrochemical capacitance of the high surface-area electrodes with respect to the electrochemical capacitance of the low surface-area electrodes), the solution volume, and the cumulative charge applied. Using a particular surface area of the high surface area electrodes and a particular (often pre-determined) solution volume, and by charging to the maximum electrochemical capacitance of the high surface-area electrodes, the cell can be constrained to produce the hypohalous acid around a particular or predetermined pH. The inventors have determined that a pH of around 2.8 (2.6 to 3.0, 2.7 to 3.0, or 2.7 to 2.9) may be optimal for the active hypochlorous acid, particularly for skin disinfection applications.

After the electrochemical sprayer is connected to the power source, typically for up to 2 minutes, a low pH environment (e.g., pH=3) is achieved, and the solution produced contains concentrated hypochlorous acid. The on-board CPU may be adapted to control the display (e.g., to activate the green light) after calculating the cumulative charge consumption.

The CPU may be advantageously adapted to count the (cumulative) charge delivered between the electrodes over the time period of the $1^{st}$ operative mode ($\Delta Q$), for example, using the equation:

$$\Delta Q = V \cdot F (10^{-pH(desirable)} - 10^{-pH(initial)})$$

where F is the Faraday constant, and V is the volume of the solution. The CPU may be advantageously further adapted to trigger or initiate the 2nd operative mode based on such a charge calculation, particularly when using a predetermined solution volume, or a solution volume within a particular range.

Once the device enters the $2^{nd}$ operative mode, the current may be appreciably lowered, typically by tenfold. The CPU (in this $2^{nd}$ operative mode) may apply a maximal voltage of around 2 Volts. Once the volume of the solution decreases, the voltage will tend to increase (due to the nominal surface area of the electrode decreases). Consequently, the CPU may control the magnitude of the current such that the voltage does not exceed an undesired or otherwise predetermined value.

As disclosed hereinabove, at such a low pH, the hypochlorous acid is not stable, such that the concentration of hypochlorous acid drops with time. The inventors have found that by applying a relatively low current (e.g., via the on-board battery), after the high surface-area electrodes are "filled" with counter-ions, the high surface-area electrodes cannot continue to function in a capacitive mode, and begin to function in a faradaic mode. Thus, while maintaining a very low current between the low and high surface area electrodes, a target pH may be substantially sustained. In the faradaic mode, both electrodes break, or react with, the solution: the low surface-area electrodes produce $H^+$ ions and the high surface-area electrodes produce $OH^-$ ions; these react with the $H^+$ ions to produce water. It must be emphasized, however, that the low surface-area electrodes also create hypochlorite ions that are converted to hypochlorous acid. Consequently, maintaining such a low current replenishes the hypochlorous acid and makes up for the hypochlorous acid depleted over time, such that the concentration of hypochlorous acid in the solution of the electrochemical device or sprayer may be substantially constant over time, even at low pH values at which the hypochlorous acid is unstable.

It must be further emphasized that the electrochemical devices and methods of the present invention may be particularly efficacious in the disinfection of various working (and other inanimate) surfaces in hospitals and kitchens, such as counters, tables, and doorframes. The portable embodiments of these electrochemical devices and methods enable such disinfection to be effected with ease.

The electrochemical devices and methods of the present invention may be particularly efficacious in the treatment and disinfection of filters in water flow paths and water treatment devices. Such filters are known to encourage biofilm formation. Moreover, treating the filters with low-pH solutions, as described herein, may also appreciably enhance the removal of scale and the like, which, in turn, yet further enhances removal of the biofilm.

One method of regenerating the negative electrode of the electrochemical sprayer is to dry the negative, high-surface electrode after rinsing out the concentrated solution with water, e.g., tap water (to avoid fouling reactions). When the high-surface electrode is dry, the adsorbed counter-ions are released, thereby reducing the electric charge on the surface of the electrode.

In one embodiment, the electrochemical sprayer utilizes a graphite electrode as the lower surface area electrode, and an activated carbon sheet, or a graphite sheet coated with activated carbon, as the high surface area electrode.

Figure 9:
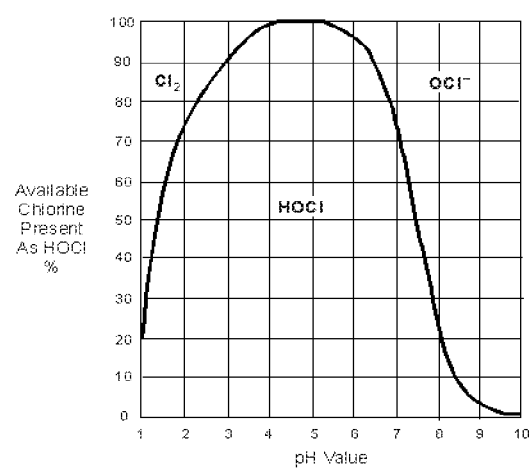
FIG. 9 is an equilibrium plot of available chlorine present as hypochlorous acid (HOCl), as a function of pH.

FIG. 9 is an equilibrium plot of available chlorine present as hypochlorous acid (HOCl), as a function of pH. It may be seen that the hypochlorous acid is most stable when the pH is within a range of 4 to 5. At pH 2, where the hypochlorous acid is the most active, only about 70% of the chlorine in the system exists as hypochlorous acid, with the remaining 30% existing as active chlorine. It is thus evident that HOCl is not stable in acidic media. Consequently, the acidic/oxidative electrolyzed water product is best used immediately and cannot be stored for long periods of time.

Figure 6:
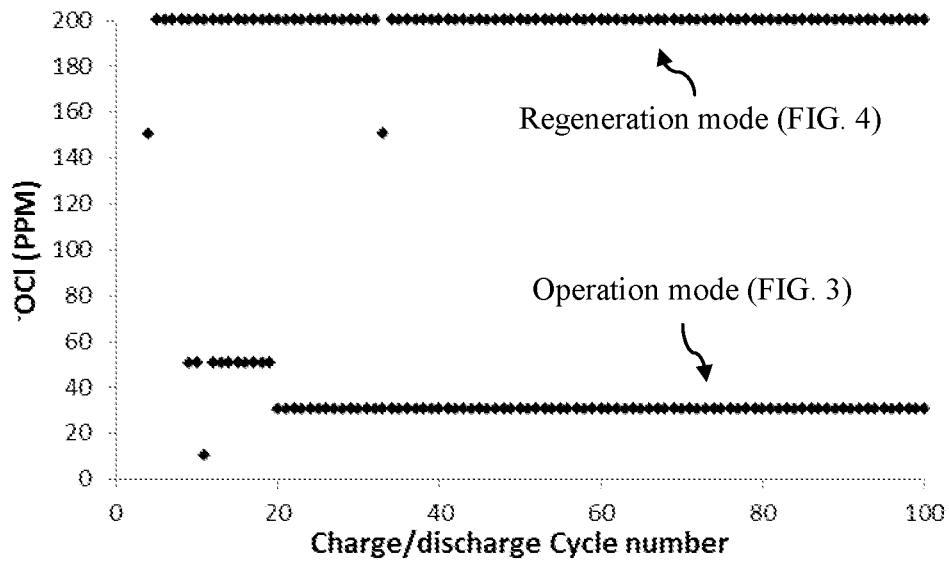
FIG. 6 is a plot of hypochlorous anion (OCl⁻) concentration as a function of the charge-discharge cycle number under constant current, applied to an inventive asymmetric towel after wetting with tap water.

FIG. 6 plots hypochlorous anion ($OCl^-$) concentration as a function of the charge-discharge cycle number under constant current, applied to an inventive electrochemical sprayer containing a 1M solution of NaCl. Periodically, the low surface area carbon cloth was positively polarized, using a constant current, up to a potential difference above 4 Volts (with respect to a reference electrode, in tap water), for 6 minutes, followed by negative polarization for 2 minutes, to obtain a neutral environment around the electrode, until the next polarization cycle. It can be observed that the electrode exhibits a substantially steady-state behavior over 100 cycles.

Figure 7:
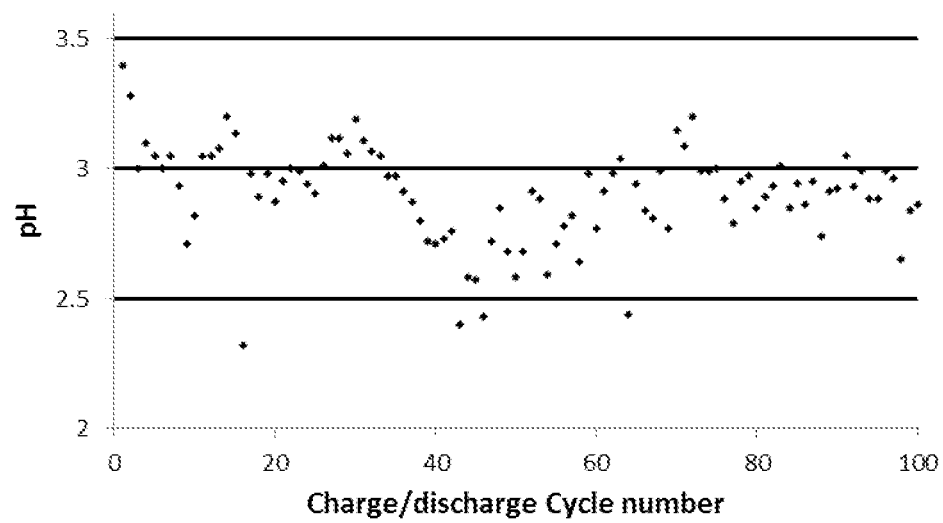
FIG. 7 is a plot of acidic pH development in the towel (low surface carbon side) as a function of time (charge-discharge cycle number)

FIG. 7 is a plot of acidic pH development in the sprayer (low surface area carbon cloth) as a function of time (charge-discharge cycle number). The power source was controlled by the on-board CPU to apply a potential of 5 Volts.

Figure 8:
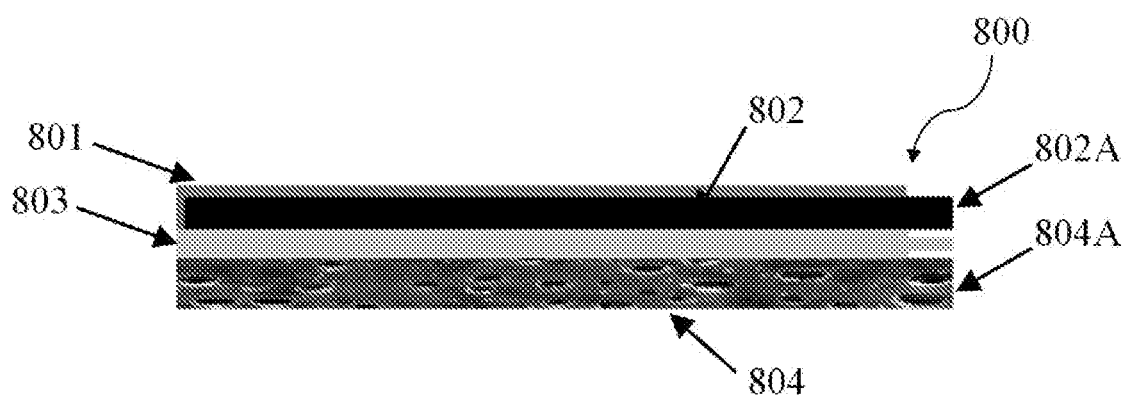
FIG. 8 is a schematic representation of an electrochemical towel, according to an embodiment of the present invention.

FIG. 8 is a schematic cross-section of an electrochemical towel 800, according to an embodiment of the present invention. While the description relates to sodium chloride in exemplary fashion, it will be appreciated that any alkali halide, or mixture of such halides, can be used. Electrochemical towel 800, which includes at least one asymmetric electrochemical cell, may have at least one high-capacitance "counter" electrode 804 and at least one low-capacitance, "working" electrode 802, separated by an insulating layer or sheet 803. Electrodes 804 and 802 may advantageously be sheet-shaped. High-capacitance electrode 804 may be made of, predominantly include, or include, activated carbon (e.g., carbon cloth). Low-capacitance electrode 802 may be made of, predominantly include, largely include, or include, graphite sheets, carbon cloth, carbon paper, or titanium metallic sponge. Electrodes 804 and 802 may have tabs or protrusions 804A, 802A that facilitate electrical connection to a power supply such as a battery (not shown). Working electrode 802 may be wrapped or covered by a cloth 801, so as to avoid mechanical abrasion on working electrode 802.

The low surface area working electrodes may be made of carbon cloth, carbon paper, graphite sheets or titanium metallic sponge. For the counter-electrodes possessing the high surface area, activated carbon cloth may advantageously be used.

In one exemplary electrochemical towel of the present invention, a commercial carbon cloth (El-Gad, Israel) was used for low-capacitance electrode 802, and a high-surface carbon cloth having a specific surface area of about 1500 $m^2/g$ (Kynol, Japan) was used for high-capacitance electrode 804. Such carbon cloth materials are made of carbon fibers.

Practical electrochemical towels 800 may have a water-resistant and corrosion-resistant control panel.

In order to prepare the towel for use, electrochemical towel 800 may be submerged in tap water, using the limited amount of NaCl (or other alkali halide) therein (typically several hundred ppm) to form the necessary reactive reagents.

Briefly, low-capacitance electrode 802 may be dimensioned so as to undergo faradaic processes during cells polarization up to 5 Volts, whereas high-capacitance electrode 804 may be dimensioned to adsorb counter ions by electrostatic interactions in a capacitive manner. By changing the potential and charging time, the pH and the concentration of the hypochlorous acid thus formed may be controlled.

Since the chlorine moieties in the towel are produced in-situ, the amount of active chlorine, as HOCl, can be adjusted to be optimal. HOCl may react with organic contaminants present in the water. Some of the products could conceivably be harmful. However, by wetting the towel through the high-surface area carbon side, such organic contaminants may be adsorbed/removed, so as to appreciably reduce any concentration of organic contaminants in the electrolyzed water. Moreover, any amount of organic contaminants produced should be very small, because tap water is used, and this is coupled with the fact that only a very small amount of water per sample/treatment is used.

Figure 10:
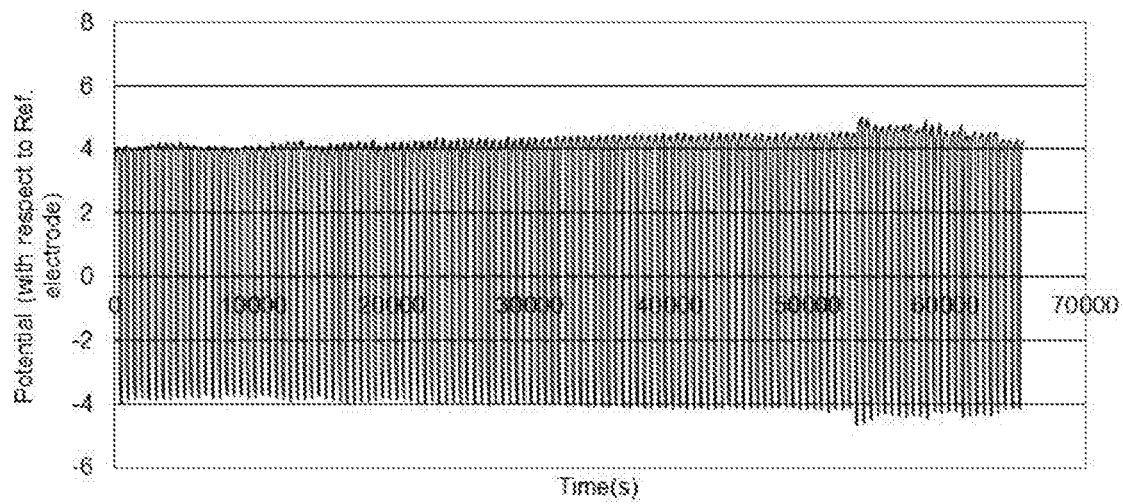
FIG. 10 is a plot of potential vs. time for an electrochemical towel, according to an embodiment of the present invention.

FIG. 10 is a plot of potential vs. time for an electrochemical towel, according to an embodiment of the present invention. The potential, measured with respect to a reference electrode, is extremely steady at about 4 Volts, for multiple cycles having a total duration in excess of 15 hours.

Figure 11:
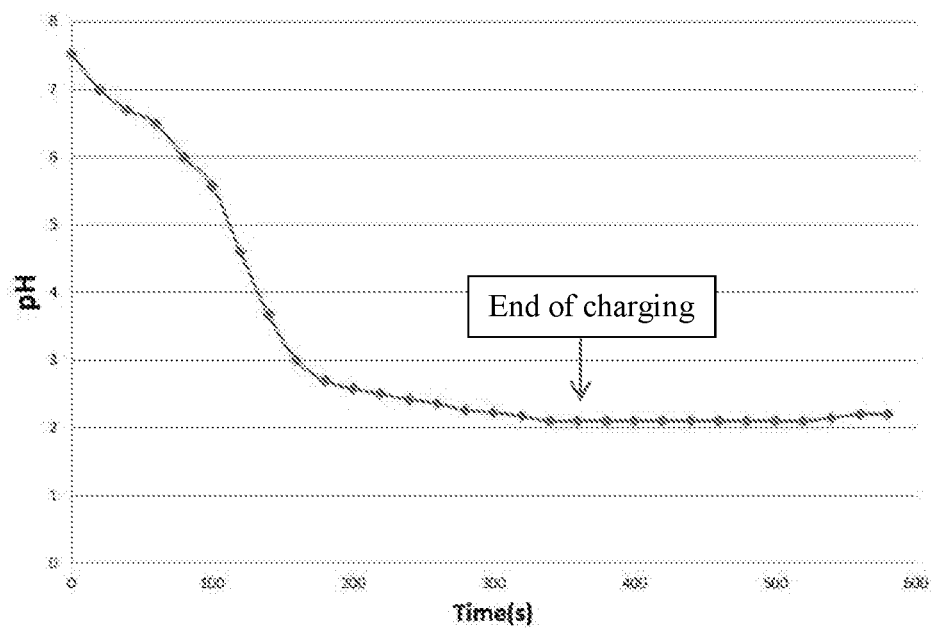
FIG. 11 is a plot of the pH development in the towel (high surface side) as a function of time, according to an embodiment of the present invention, in which the semi-capacitive mode is effected for the first 320 seconds.

FIG. 11 is a plot of the pH development in a rectangular, 8×16 cm towel (low surface-area side) as a function of time, according to an embodiment of the present invention, in which the semi-capacitive mode is effected for the first 340 seconds. The power source was controlled by the on-board CPU to apply a potential of 5 Volts. The pH of the towel surface was monitored using a surface pH meter (Orion). After about 150 seconds, the acidity upon the surface of the towel had dropped to a pH of around 3. After 340 seconds, the application of the potential was ceased and the pH remained quite steady (around 2.1) during the remaining 3 minutes of the run.

Figure 12:
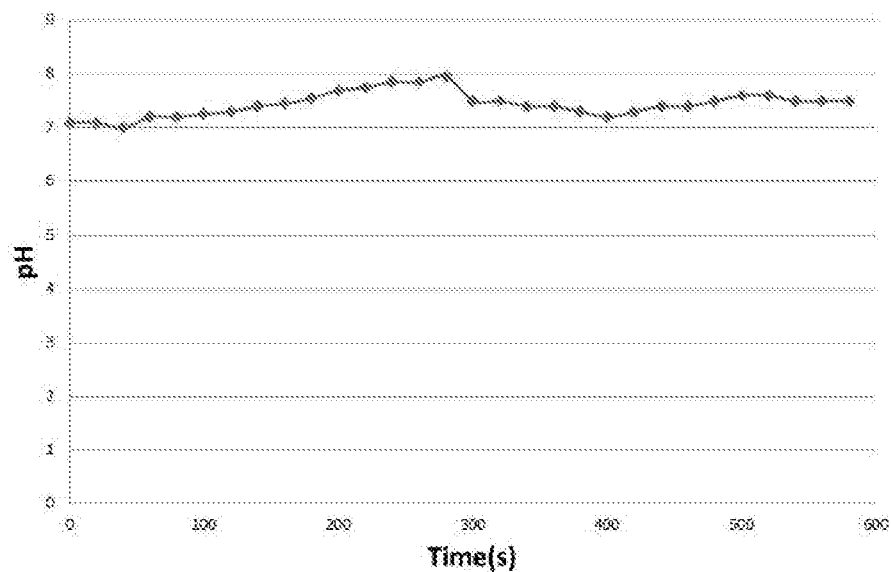
FIG. 12 is a plot of the pH development in the towel (high surface side) as a function of time, according to an embodiment of the present invention.

FIG. 12 is a plot of the pH development in the towel (high surface-area side) as a function of time, using the identical time scale of FIG. 11. The power source was controlled by the on-board CPU to apply a potential of 5 Volts. No major changes in the pH were observed, apparently because the main process transpiring was the adsorption of cations.

Figure 13:
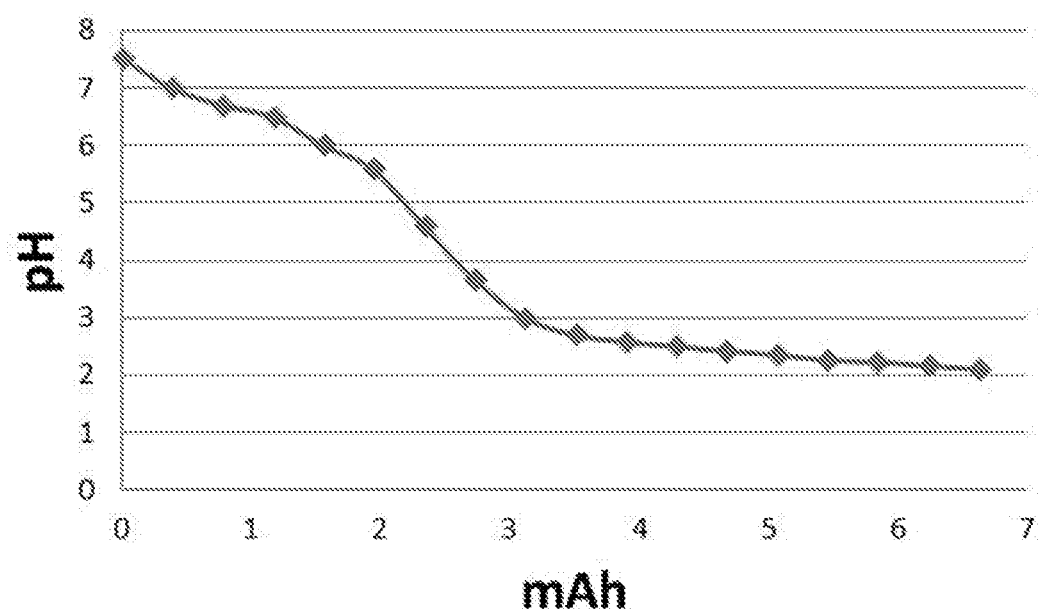
FIG. 13 is a plot of the pH development in the towel, as a function of total charge consumption, according to an embodiment of the present invention.

FIG. 13 is a plot of the pH development in the towel, as a function of the total charge consumption, according to an embodiment of the present invention. The power source was controlled by the on-board CPU to apply a potential of 5 Volts.

Figure 14:
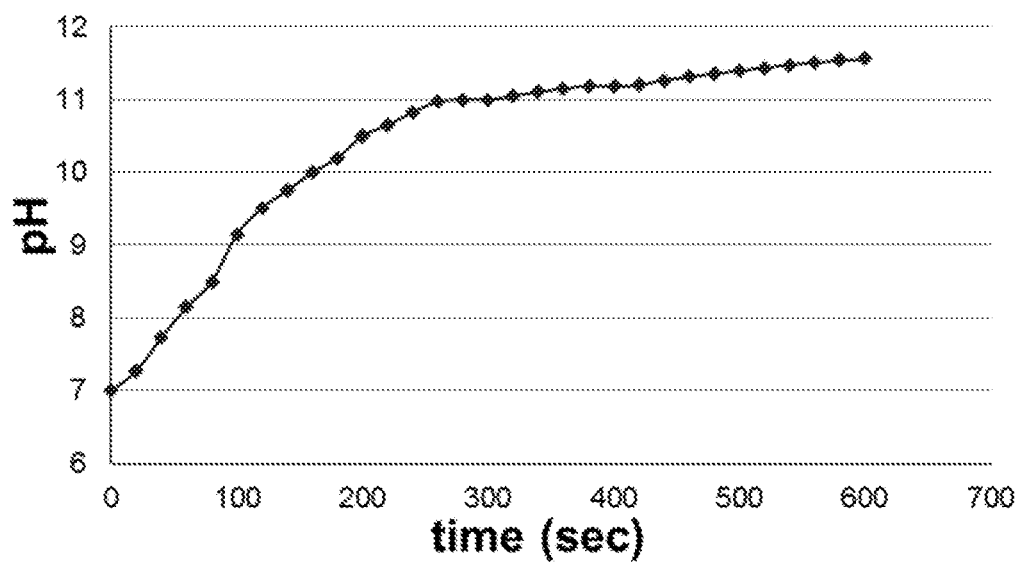
FIG. 14 is a plot of the pH development in the towel (low surface side) as a function of time, according to an embodiment of the present invention.

FIG. 14 is a plot of the pH development in the towel surface as a function of time, during a regeneration (or alkaline solution production) stage, according to an embodiment of the present invention. The power source was controlled by the on-board CPU to apply a potential of 5 Volts. By negative polarization of the towels (or similarly, with the electrochemical sprayer) high pH values may be attained. Electrolyzed water having such high pH values may be particularly suitable for surface treatments. In this example, a rectangular, 8×16 cm towel (carbon cloth) was used. A potential difference of −5V was applied to the towel, and the pH of the towel surface was monitored using a surface pH meter (Orion). It may be observed that a highly basic (pH>11) environment on the surface of the towel was attained after about 5 minutes.

The anti-microbial efficacy of the inventive electrochemical towels having absorbed hypohalous solution was tested on colonies of i Staphylococcus Aureus and *E. Coli*. The colonies were grown to a concentration of about 10,000 microbes/ml on Petri plates. Mini-electrochemical towel pads (1.5 cm×1.5 cm) were produced for this purpose. The pads were soaked in tap water (containing several hundred ppm of sodium chloride solute) and were pre-charged to 5V for 3 minutes. The pads were then placed on top of the respective bacteria colonies, in the middle of each Petri dish, for another 3 minutes of charge under 5V.

FIGS. 15A and 16A are photographs of Escherichia coli (FIG. 15A) and Staphylococcus Aureus (FIG. 16A) colonies in Petri dishes, grown as reference colonies for a period of 24 hours. Unpolarized pads, soaked in tap water, had been placed on top of the reference bacteria colonies.

FIGS. 15B and 16B are photographs of the Escherichia coli (FIG. 15B) and Staphylococcus Aureus (FIG. 16B) colonies, following treatment in the central area of the cultures, using polarized mini-towels (carbon mini-pads) of the present invention. The mini-towels were prepared by soaking them in tap water, followed by effecting the semi-capacitive and faradaic stages, as described hereinabove.

It may be seen that after the identical 24-hour period, a central region in each of the bacteria cultures is substantially devoid of bacteria, for both the *Escherichia coli* (FIG. 15B) and the *Staphylococcus Aureus* (FIG. 16B).

By contrast, in the central region of each reference colony, no void regions were observed, indicating that the polarization of the tap water soaked in the mini towels was the cause behind the inhibited growth of the bacteria colonies.

Figure 17A:
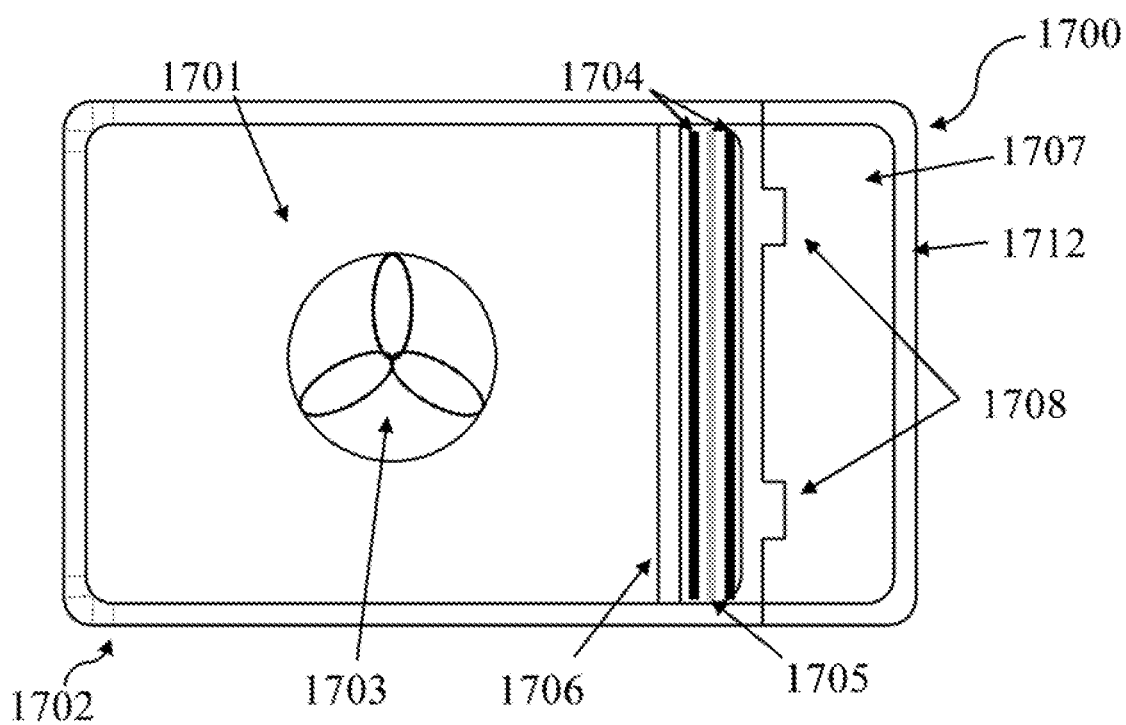
FIG. 17A provides a schematic, transparent top view of an electrochemical container, according to an embodiment of the present invention.
Figure 17B:
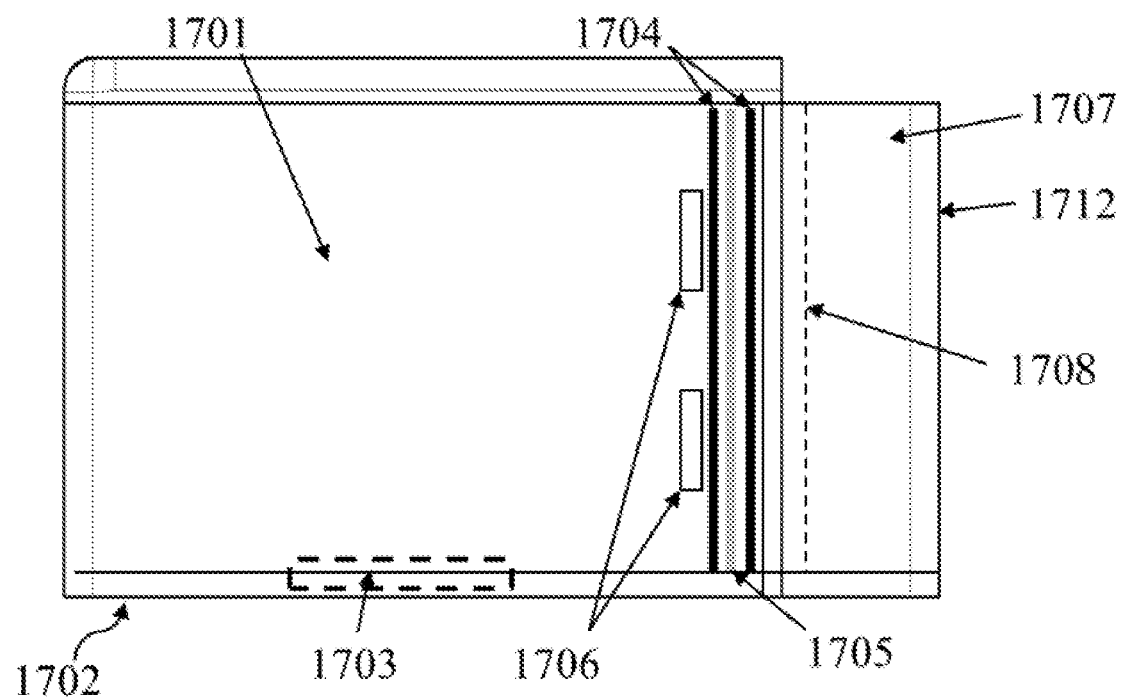
FIG. 17B provides a schematic, transparent side view of the electrochemical container of FIG. 17A.

FIG. 17A provides a schematic, transparent top view of an asymmetric electrochemical device or container 1700, according to an embodiment of the present invention, and FIG. 17B provides a schematic, transparent side view of this device or container.

Within the container or vessel 1702 portion of electrochemical device 1700 are disposed at least one high surface-area electrode 1704 and at least one low surface-area electrode 1705. Electrodes 1704 and 1705 may be arranged as sheets, typically substantially parallel sheets, disposed in a vertical orientation with respect to the side of vessel 1702, as shown in FIG. 17A.

Electrochemical device 1700 has a pool or container compartment 1701, generally defined by a pool casing or housing 1702, and an electronics unit or compartment 1707, generally defined by an electronics casing or housing 1712, and typically disposed at the side of container compartment 1701. It will be appreciated that casing 1712 may be distinct and fluidly sealed with respect to the liquid contents within pool casing 1702.

Electronics unit 1707 of inventive electrochemical container 1700 typically includes a CPU and associated memory, at least one switch or switching mechanism, a power supply, a display, and a power source port, and may be substantially identical to the electronic unit provided in FIG. 5C and described hereinabove. In some embodiments, however, a battery may be unnecessary.

Within pool compartment 1701 may be disposed a stirring mechanism 1703, which is typically anchored in a bottom surface of pool compartment 1701. Stirring mechanism 1703, which may be adapted to obtain a substantially homogeneous mixture of active product in the aqueous solution within pool compartment 1701, may be electrically connected to, and powered by electronics unit 1707.

A casing wall 1708 of electronics unit 1707, disposed between electronics unit 1707 and container compartment 1701, may be used to secure the electronics (e.g., disposed on an electric board) in place, for example, using screws or other securing hardware.

A casing component such as partition 1706 may be used to hold the electrodes in place, and may have ports or holes to facilitate the transport of fluid in the vicinity of the electrodes.

Electrochemical container 1700 may be operated substantially as described hereinabove, particularly with respect to FIGS. 3 and 4. In one particular embodiment, electrochemical container 1700 may be operated such that, in a first stage, the first, negative electrode operates in a capacitive mode, while the second, positive electrode operates in a faradaic mode (e.g., providing a low pH, disinfecting environment) and in a second (preceding or subsequent) stage, the polarity is reversed, such that the second (now negative) electrode operates in a faradaic mode, while the first (now positive) electrode operates in a capacitive mode, producing highly alkaline electrolyzed water (e.g., so as to remove pesticides from the surface of goods or agricultural produce immersed within the alkaline electrolyzed water produced and disposed in vessel 1702). Typically, it is the CPU that effects the reversing of polarity, for example, by controlling a switching mechanism associated with the electrodes.

As used herein in the specification and in the claims section that follows, the term "electrochemical capacitance", with respect to an electrode, is generally defined by:

$$C=Q/E,$$

where C is the electrochemical capacitance (in F/g), Q is the charge (in coulombs) and E is the potential difference (in Volts) of the electrode with respect to a reference electrode. When possible, the electrochemical capacitance is yet more accurately calculated using the equation:

$$Cd=dQ/dE,$$

where Cd is the differential electrochemical capacitance,

Quantitative measurement of "electrochemical capacitance" is performed by cyclic voltammetry, as is known to those of skill in the art, and specifically, as disclosed by B. E. Conway, Electrochemical Supercapacitors: Scientific Fundamentals and Technological Applications (Kluwer Academic/Plenum Publishers, New York, N.Y. (1999)), which is hereby incorporated by reference for all purposes as if fully set forth herein.

In cyclic voltammetry, the potential of the electrode (with respect to a reference electrode) is linearly scanned (usually starting from the initial immersion potential, which may be denoted as potential of zero charge (PZC) back and forth. The output is the current (vertical axis) versus the potential. Since the scan rate (dE/dt) is constant and the current (I) equals dQ/dt (t=time), dividing the current values from the vertical axis by the scan rate value provides the differential capacitance (Cd) with respect to the potential (i.e., Cd(E)). A more detailed description of such a conventional technique is disclosed by Conway.

As used herein in the specification and in the claims section that follows, the term "portable" with respect to an electrochemical device or cell, refers to a device or cell that can be freely ported, or freely moved around, by a user, while functioning in an operative, electrochemical mode using an On-board or other cordless power supply.

As used herein in the specification and in the claims section that follows, the term "percent", or "%", refers to percent by weight, unless specifically indicated otherwise.

Similarly, the term "ratio", as used herein in the specification and in the claims section that follows, refers to a weight ratio, unless specifically indicated otherwise.

As used herein in the specification and in the claims section that follows, the term "largely includes", with respect to a component within a formulation, refers to a weight content of at least 30%, at least 40%, at least 50%, or at least 60%.

As used herein in the specification and in the claims section that follows, the term "mostly includes", with respect to a component within a formulation, refers to a weight content of at least 50%.

As used herein in the specification and in the claims section that follows, the term "predominantly includes", with respect to a component within a formulation, refers to a weight content of at least 60%, at least 70%, or at least 85%.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, including U.S. Provisional Patent Application Ser. No. 62/209,399, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A towel, comprising:
   (a) at least a first electrode layer covered by a cloth suitable to reduce mechanical abrasion;
   (b) at least a second electrode layer;
   (c) an electrically insulating layer disposed in between said first electrode layer and said second electrode layer; at least one of said first electrode layer, said electrically insulating layer, and said second electrode layer being adapted to absorb a liquid;
   (d) connectors to facilitate connection of said first electrode layer and said second electrode layer to a power supply; and
   (e) an electrochemical capacitance ratio ($R_{ec}$) of said at least a first electrode layer to said at least a second electrode layer of at least 7:1.

2. The towel as claimed in claim 1, wherein the first electrode layer comprises activated carbon.

3. The towel as claimed in claim 1, wherein the second electrode layer comprises a construct selected from a graphite sheet, a carbon cloth, a carbon paper and a titanium cloth.

4. An assembly comprising:
   A towel as claimed in claim 1, and a power supply connected to said connectors, said power supply adapted to apply an electrical current between said first and second electrode layers.

5. The assembly as claimed in claim 4 comprising a processor adapted to reverse a polarity of said electrical current.

6. A method comprising:
   wetting a towel in the assembly of claim 4 with tap water;
   applying an electrical current between said first and second electrode layers using said power supply;
   wherein said current generates hypohalous acid from said tap water.

7. The method according to claim 6, comprising wiping a surface with said towel so that said hypohalous acid exerts an antimicrobial effect on said surface.

8. An asymmetric electrochemical cell comprising:
   (a) at least a first electrode layer;
   (b) at least a second electrode layer;
   (c) an electrochemical capacitance ratio ($R_{ec}$) of the first electrode layer to the second electrode layer of at least 3:1;
   (d) a housing adapted to contain the first and the second electrodes such that they are immersed in an aqueous solution during use;
   (e) a processor; and
   (f) a power supply;
   wherein the electrodes are connected to the opposite poles of the power supply, and wherein the processor and the power supply are adapted to apply a first electric current between said first and said second electrodes layers during a first mode and a second electric current during a second mode, suitable to produce hypohalous acid from a solution containing alkali metal cations and halogen anions.

9. The asymmetric electrochemical cell according to claim 8, installed in a vessel equipped with a spraying head operable to spray a liquid contained in said vessel.

10. The asymmetric electrochemical cell according to claim 8, wherein the second electrode layer comprises a construct selected from a graphite sheet, a carbon cloth, a carbon paper and a titanium sponge.

* * * * *